United States Patent [19]

Williams et al.

[11] Patent Number: 4,481,957

[45] Date of Patent: Nov. 13, 1984

[54] SMOKING COMPOSITIONS CONTAINING NOVEL ACYLPYRAZINE FLAVORANTS

[75] Inventors: David L. Williams; Everett W. Southwick; Yoram Houminer, all of Richmond, Va.

[73] Assignee: Philip Morris, Incorporated, New York, N.Y.

[21] Appl. No.: 421,922

[22] Filed: Sep. 23, 1982

[51] Int. Cl.³ .................... A24B 3/12; A24B 15/38
[52] U.S. Cl. .................................................. 131/278
[58] Field of Search ................ 131/275, 276, 277, 278

[56] References Cited

U.S. PATENT DOCUMENTS

| | | | |
|---|---|---|---|
| 3,402,051 | 9/1968 | Roberts | 99/140 |
| 3,764,349 | 10/1973 | Mookherjee et al. | 426/65 |
| 3,881,025 | 4/1975 | Flament | 426/537 |
| 3,890,320 | 6/1975 | Wolt | 260/250 B |
| 3,914,227 | 10/1975 | Pittet et al. | 260/250 B |
| 3,917,872 | 11/1975 | Winter et al. | 426/537 |

OTHER PUBLICATIONS

Caronna et al., J. Chem. Soc. Perkin II, 1972, 2035-2036;8.
Schumacher et al., J. Agr. Food Chem., 25(2), (1977), 310-312, 315-317.

*Primary Examiner*—V. Millin
*Attorney, Agent, or Firm*—Arthur I. Palmer; James E. Schardt

[57] ABSTRACT

In one of its embodiments the present invention provides a smoking composition which contains a novel type of bicyclic acylpyrazine flavorant additive as exemplified by 2-acetyl-5,6,7,8-tetrahydrocyclohexa[b-]pyrazine:

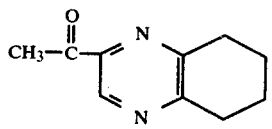

9 Claims, No Drawings

SMOKING COMPOSITIONS CONTAINING NOVEL ACYLPYRAZINE FLAVORANTS

BACKGROUND OF THE INVENTION

An important advance in the tobacco industry is the development of novel types of flavorant additives for incorporation in smoking compositions, as a consequence of the increasing demand for low delivery filter cigarettes.

Alkylpyrazines are typical of organic compounds which have been recognized as having useful properties for application as flavorants in tobacco and foodstuffs. Various species have been identified in natural products as flavorant or fragrance constituents.

Unlike alkylpyrazines which are ubiquitous in nature and heat-treated foodstuffs, acylpyrazines are more limited in their occurrence. For example, 2-acetyl-5-methylpyrazine and 2-acetyl-5-ethylpyrazine are reported as constituents of cocoa in Tabacco International, page 18ff (March 1979), and 1-(2-pyrazinyl)-1-butanone is tentatively identified as a water-soluble component of cigarette smoke in J. Agric. Food Chem., 25(2), 310 (1977).

Several acetylpyrazines are included in the F.E.M.A. listing of food additives as being useful for imparting a popcorn-nutty flavor to a foodstuff. The incorporation of acetylpyrazine, 2-acetyl-5-methylpyrazine or 2-acetyl-6-methylpyrazine as a popcorn-like flavorant in foodstuffs and tobacco is described in U.S. Pat. No. 3,402,051.

Interest in pyrazines as flavorants or fragrances has stimulated the investigation of various types of substituted pyrazines which potentially have unique organoleptic properties.

Bicyclic pyrazines are described in U.S. patents which include U.S. Pat. Nos. 3,636,177; 3,702,253; 3,748,145; 3,764,349; and 3,968,212. U.S. Pat. No. 3,705,121 discloses tricyclic pyrazine derivatives. Illustrative of polycyclic pyrazines are 5,6,7,8-tetrahydroquinoxaline and 1,2,3,4, 6,7,8,9-octahydrophenazine:

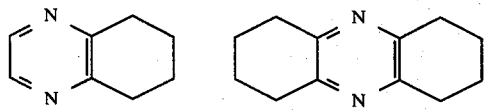

There is continuing research effort to develop new types of heterocyclic compounds which exhibit useful flavorant or fragrance properties.

Accordingly, it is an object of this invention to provide a novel class of acylpyrazine compounds which exhibit unique properties for application as flavorants.

It is a further object of this invention to provide smoking compositions of tobacco and non-tobacco materials containing a bicyclic acylpyrazine flavorant additive, which smoking compositions are adapted to impart flavor and aroma to mainstream and sidestream smoke under smoking conditions.

Other objects and advantages of the present invention shall become apparent from the accompanying description and disclosure.

DESCRIPTION OF THE INVENTION

One or more objects of the present invention are accomplished by the provision of a smoking composition comprising an admixture of (1) combustible filler selected from natural tobacco, reconstituted tobacco, non-tobacco substitutes, and mixtures thereof, and (2) between about 0.00001 and 2 weight percent, based on the total weight of filler, of a bicyclic acylpyrazine corresponding to the formula:

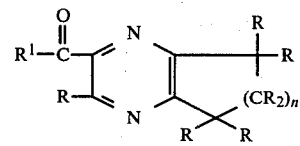

where R is a substituent selected from hydrogen and alkyl groups containing between about 1–12 carbon atoms; $R^1$ is a substituent selected from aliphatic, alicyclic and aromatic groups containing between about 1–20 carbon atoms; and n is an integer in the range of 1–6.

Illustrative of the R substituents in the represented acylpyrazine formula are groups which include methyl, ethyl, butyl, heptyl, 2-ethylhexyl, decyl, dodecyl, and the like.

Illustrative of the $R^1$ substituent in the represented acylpyrazine formula are groups which include methyl, ethyl, propyl, butyl, pentyl, hexyl, methoxyethyl, ethoxyethyl, cyclopropyl, cyclobutyl, cyclopentyl, cyclohexyl, menthyl, furyl, tetrahydrofuryl, phenyl, tolyl, xylyl, benzyl, phenylethyl, methoxyphenyl, pyridyl, pyrazyl, and the like.

PREPARATION OF BICYCLIC ACYLPYRAZINES

Various specific methods of synthesizing acylpyrazine derivatives are disclosed in U.S. patents such as U.S. Pat. Nos. 3,711,482; 3,767,428; 3,890,320; and 3,914,227; and the like.

In J. Chem. Soc., Perkin II, 2035 (1972) there is reported the acylation of protonated pyrazine derivatives. In a general procedure, a heteroaromatic compound (e.g., pyrazine) is acylated by reacting the compound with alkanal in the presence of t-butyl hydroperoxide and iron(II) sulfate in a homogeneous aqueous medium of acetic acid and sulfuric acid.

An efficient method for preparation of the present invention bicyclic acylpyrazine compounds is that disclosed in copending patent application Ser. No. 307,262, incorporated herein by reference. The process described is suitable for acylation of either pyrazines or polycyclic pyrazines. The said process involves the steps of (1) providing a heterogeneous reaction medium consisting of a water-immiscible organic phase and an acidic aqueous phase, wherein the organic phase comprises a mixture of an aldehyde compound (RCHO) and a pyrazine compound corresponding to the formula:

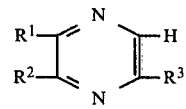

where $R^1$, $R^2$ and $R^3$ are substituents selected from hydrogen and alkyl groups, and $R^1$ and $R^2$ when taken together with connecting elements form an alicyclic or aromatic structure, and R in the aldehyde compound is a substituent selected from aliphatic, alicyclic and aromatic groups; (2) maintaining efficient contact between the organic and aqueous phases for a period of time sufficient to achieve acylation of the pyrazine compound in the presence of a free radical generating agent; and (3) recovering a monoacylpyrazine product corresponding to the formula:

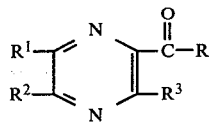

where R, $R^1$, $R^2$ and $R^3$ are substituents as previously defined.

The aldehyde (R—CHO) reactant can be any compound which does not contain any substituents which inhibit or prevent the free radical interaction of the aldehyde functionality with the pyrazine nucleus. It is preferred that the aldehyde reactant is at least partially soluble in the aqueous phase of the acylation system, in order to increase the rate and efficiency of the acylation reaction.

When taken together with connecting elements, $R^1$ and $R^2$ can form an alicyclic or aromatic structure. Illustrative of this type of pyrazine derivative are quinoxaline and 5,6,7,8-tetrahydroquinoxaline:

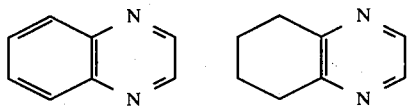

The pyrazine and aldehyde reactants can be employed over a wide range of molar ratios. It has been found convenient and advantageous to employ a molar ratio between about 0.5-10:1 of aldehyde to pyrazine in the acylation system.

The relative volumes of the respective immiscible phases in the acylation system are not critical, and typically the two phases will be approximately equal in volume.

The acidity of the aqueous phase is provided by the addition of a suitable acid reagent such as sulfuric acid, hydrochloric acid, phosphoric acid, and the like. The pH of the aqueous phase is below about 6, and preferably is in the range between about 1-5.

The acylation reaction between the pyrazine and aldehyde reactants is catalyzed by the inclusion of a free radical generating agent, in a quantity between about 1-50 weight percent, based on the weight of aldehyde reactant.

Illustrative of suitable free radical initiators are hydrogen peroxide; alkali metal or ammonium persulfates, perborates, peracetates and percarbonates; organic peroxides and hydroperoxides such as benzoyl peroxide, t-butylhydroperoxide and diisopropylperoxydicarbonate; and the like. The initiator may be associated with activating means (e.g., a redox system) which involves the use of compounds such as sulfites and thiosulfites, and redox reaction promoters such as transition metal ions (e.g., $Fe^{++}$).

PREPARATION OF TOBACCO COMPOSITIONS

The present invention smoking compositions can be prepared by admixing natural tobacco and/or reconstituted tobacco and/or a non-tobacco substitute with between about 0.00001 and 2 weight percent, and preferably 0.0001-2 weight percent, based on the weight of the smoking composition, of a flavorant additive which corresponds to one of the structural formulas set forth hereinabove in definition of the bicyclic acylpyrazine compounds.

An invention bicyclic acylpyrazine flavorant additive can be incorporated into the tobacco in accordance with methods known and used in the art. Preferably the flavorant additive is dissolved in a solvent such as water, alcohol, or mixtures thereof, and then sprayed or injected into the tobacco or non-tobacco substitute matrix. Such method ensures an even distribution of the flavorant additive throughout the tobacco, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or non-tobacco substitute filler in a concentration between about 0.5-5 weight percent, based on the weight of filler, and then subsequently to blend the treated filler with filler which does not contain flavorant additive.

The term "non-tobacco substitute" is meant to include smoking filler materials such as are disclosed in U.S. Pat. Nos. 3,529,602; 3,703,177; 3,796,222; 4,019,521; 4,079,742; and references cited therein; incorporated herein by reference.

Illustratively, U.S. Pat. No. 3,529,602 describes a burnable sheet which may be used as a tobacco substitute, which sheet contains ingredients which include (1) a film-forming ingredient comprising a pectinaceous material derived from tobacco plant parts and having an acid value in excess of 30 milligrams of potassium hydroxide per gram, and (2) a mineral ingredient comprising an alkali metal salt, an alkaline earth metal salt or clay.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°-750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

When a present invention bicyclic acylpyrazine is incorporated into smoking material as a flavorant additive, and cigarettes are manufactured from the flavored blend, under smoking conditions the cigarettes have an increased flavor amplitude and/or other desirable properties in comparison with control cigarettes which do not contain an invention acylpyrazine flavorant additive, as illustrated in Example VII.

The following examples are further illustrative of the present invention. The reactants and other specific ingredients are presented as being typical, and various modifications can be derived in view of the foregoing disclosure within the scope of the invention.

EXAMPLE I

Preparation Of 2-Acetyl-5,6,7,8-tetrahydroquinoxaline

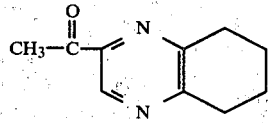

To a stirring heterogeneous mixture of freshly distilled acetaldehyde (1.32 g, 30 mmoles) and 5,6,7,8-tetrahydroquinoxaline (670 mg, 5 mmoles) in 2.5 milliliters of 3.4M sulfuric acid, at 3° C., is added concurrently 70% t-butylhydroperoxide (2.7 g, 21 mmoles) and a solution of ferrous sulfate (8.35 g, 30 mmoles) in 20 milliliters of water over a 10 minute period. The resulting heterogeneous mixture is stirred an additional 1 hour, during which time the temperature is raised to 14° C. Solid sodium sulfite is then added until test with starch-iodine paper is negative.

The aqueous layer is extracted with methylene chloride (3×50 milliliters), and the extracts are combined and washed with water. Optionally, the combined extract phase is washed with aqueous alkaline solution to remove acidic components. After drying (MgSO$_4$), the crude product is submitted to preparative thick layer chromatography (2000μ silica gel GF, developed in 5% acetone/hexane) which results in a 22% yield of 2-acetyl-5,6,7,8-tetrahydroquinoxaline as an off-white solid (m.p. 42°–45° C.).

An analytically pure sample for odor and flavor evaluation is obtained by preparative GLC (¼"×15', Carbowax ® 20M-TPA). The structure is confirmed by IR, NMR and MS spectroscopy, and by elemental analysis.

Anal. calc. for $C_{10}H_{12}N_2O$: C, 68.16; H, 6.86; N, 15.90. Found: C, 68.01; H, 6.90; N, 15.74.

EXAMPLE II

Preparation Of 2(and 3)-Propionyl-5H-5-methyl-6,7-dihydrocyclopenta[b]pyrazine

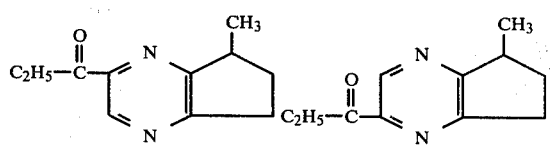

The reaction of 5H-5-methyl-6,7-dihydrocyclopentapyrazine and freshly distilled propionaldehyde is carried out on twice the molar scale described in Example I. The acylation product is obtained as a mixture of positional isomers in a yield of 24% based on the recovery of crude product.

An analytically pure sample of the isomer mixture for odor and flavor evaluation is obtained by preparative GLC (¼"×15', Carbowax ® 20M TPA polyethylene oxide). The structures are confirmed by IR, NMR and MS spectroscopy; and by elemental analysis.

Anal. calc. for $C_{11}H_{14}N_2O$: C, 69.45; H, 7.42; N, 14.72. Found: C, 69.67; H, 7.51; N, 14.91.

EXAMPLE III

Preparation Of 2-Propionyl-5,6,7,8-tetrahydro-8,9,9 (and 5,9,9)-trimethyl-5,8-methanoquinoxaline

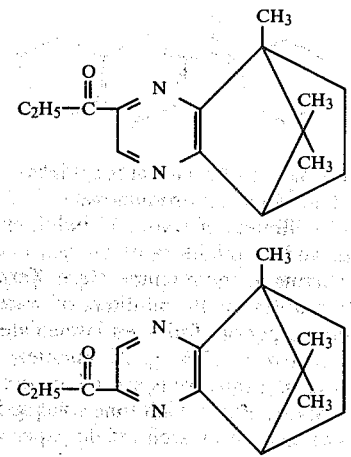

The reaction of 5,6,7,8-tetrahydro-5,9,9-trimethyl-5,8-methanoquinoxaline and freshly distilled propionaldehyde is carried out on the same molar scale as described in Example I. The reaction medium is stirred at room temperature for 1 hour. The acylation product is obtained as a mixture of positional isomers in a yield of 16% based on the recovery of crude product.

An analytically pure sample of the isomeric mixture for odor and flavor evaluation is obtained by preparative GLC (¼"×10', 5% SE-30). The structures are confirmed by IR, NMR and MS spectroscopy, and by elemental analysis.

Anal. calc. for $C_{15}H_{20}N_2O$: C, 73.73; H, 8.25; N, 11.47. Found: C, 73.55; H, 8.17; N, 11.31.

EXAMPLE IV

Preparation Of 2-Propionyl-5H,6,7,8,9-tetrahydrocyclohepta[b]pyrazine

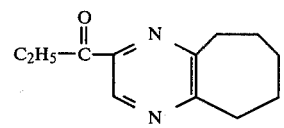

The reaction of 5H,6,7,8,9-tetrahydrocyclohepta[b]pyrazine and freshly distilled propionaldehyde is conducted at one-half the molar scale described in Example I. The crude acylated product is passed through a silica gel column in 5% acetone/hexane to give a 37% yield of ≧95% pure 2-propionyl-5H,6,7,8,9-tetrahydrocyclohepta[b]pyrazine.

An analytically pure sample for odor and flavor evaluation is obtained by preparative GLC (¼"×10', 5% SE-30). The structure is confirmed by IR, NMR and MS spectroscopy, and by elemental analysis.

Anal. calc. for $C_{12}H_{16}N_2O$: C, 70.56; H, 7.90; N, 13.71. Found: C, 70.74; H, 7.92; N, 13.71.

The substitution of cyclohexanecarboxaldehyde or benzaldehyde for propionaldehyde in the reaction yields the corresponding 2-cyclohexylcarbonyl and 2-benzoyl derivatives, respectively.

EXAMPLE V

Preparation Of
2-Cyclohexanoyl-5,6,7,8-tetrahydroquinoxaline

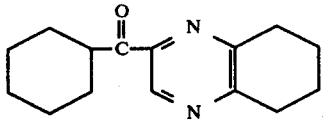

A mixture of cyclohexanecarboxaldehyde (5.6 g, 50 mmoles), 5,6,7,8-tetrahydroquinoxaline (1.34 g, 10 mmoles), 15 milliliters of water, 15 milliliters of glacial acetic acid, and 3 milliliters of concentrated sulfuric acid is set stirring at room temperature. Ferrous sulfate (5.56 g, 20 mmoles) in 10 milliliters of water is added over a 3 minute period, followed immediately by 70% t-butylhydroperoxide (2.56 g, 20 mmoles) at a rapid rate. The resulting mixture is stirred at room temperature for 1.5 hours, after which time solid sodium sulfite is added until test with starch-iodide paper is negative.

The aqueous layer is extracted with benzene 3×75 milliliters), and the combined organic extracts washed with saturated sodium bicarbonate (2×50 milliliters), water (50 milliliters) and saturated sodium chloride (50 milliliters). After drying (MgSO₄), the crude product is submitted to bulb-to-bulb distillation [oven temp. ~70° C. (0.1 mm Hg)] to remove volatiles. The pot residue is then charged to a chromatography column (25 g silica gel, developed in 5% acetone/hexene). Crystallization from methanol provides, 6% yield of pure 2-cyclohexanoyl-5,6,7,8-tetrahydroquinoxaline as a solid (m.p. 63.5°–64.5° C.). The structure is confirmed by IR and NMR spectroscopy, and by elemental analysis.

Anal. calc. for $C_{15}H_{20}N_2O$: C, 73.73; H, 8.25; N, 11.47. Found: C, 73.94; H, 8.24; N, 11.45.

EXAMPLE VI

Preparation Of
2-Benzoyl-5,6,7,8-tetrahydroquinoxaline

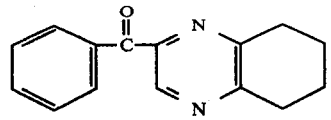

The reaction of benzaldehyde and 5,6,7,8-tetrahydroquinoxaline is carried out on the same molar scale and in the same manner as described in Example V. The crude reaction product is submitted to bulb-to-bulb distillation [oven temp. ~60° C. (0.1 mm Hg)] to remove volatiles. Column chromatography (30 g silica gel developed in 3% acetone/hexane), followed by high performance liquid chromatography (Magnum ®9, Partisil ®10, developed in 4% acetone/2,2,4 trimethylpentane) provides 6% yield of 2-benzoyl-5,6,7,8-tetrahydroquinoxaline as a solid (m.p. 61.5°–63.5° C.). The structure is confirmed by IR and NMR spectroscopy, and by elemental analysis.

Anal. calc. for $C_{15}H_{14}N_2O$: C, 75.60; H, 5.92; N, 11.76. Found: C, 75.63; H, 6.08; N, 11.60.

EXAMPLE VII

Preparation Of Present Invention Smoking Compositions Containing A Novel Acylpyrazine Flavorant Cigarettes are fabricated using a typical blend of tobaccos treated with an ethanolic solution of an acylpyrazine flavorant as listed in the Table, to provide 0.0005 percent of the compound by weight of the tobacco. Untreated control cigarettes are prepared using the identical tobacco blend, and the treated cigarettes are compared to the controls by an experienced smoking panel. The treated cigarettes are found to have the smoke flavor properties described in the Table, as compared to the controls.

TABLE

| COMPOUND | EX. | ODOR ON BLOTTER | SMOKE FLAVOR, PROPERTIES |
|---|---|---|---|
| (CH₃-C(=O)- 2-acyl-5,6,7,8-tetrahydroquinoxaline) | 1 | Popcorn-like | Sweeter, low nutty |
| (C₂H₅-C(=O)- methyl-substituted cyclopentapyrazine) | 2 | Sweet roasted-nutty | More robust, fuller smoke |
| (C₂H₅-C(=O)- bicyclic pyrazine) | 3 | a | Subdued clove-spicey |
| (C₂H₅-C(=O)- cycloheptapyrazine) | 4 | Sweet roasted | Smoother, increased flavor response |

TABLE-continued

| COMPOUND | EX. | ODOR ON BLOTTER | SMOKE FLAVOR, PROPERTIES |
|---|---|---|---|
| 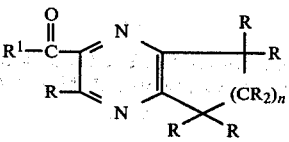 | 5 | a | Floral green (geranium) |
| 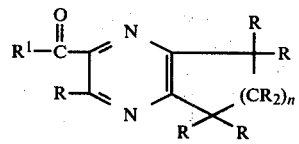 | 6 | a | Slightly phenolic | a No detectable odor at room temperature.

What is claimed is:

1. A smoking composition comprising an admixture of (1) combustible filler selected from natural tobacco, reconstituted tobacco, non-tobacco substituents, and mixtures, thereof, and (2) between about 0.00001 and 2 weight percent, based on the total weight of filler, of a bicyclic acylpyrazine corresponding to the formula:

$$R^1-\underset{\underset{O}{\parallel}}{C}-\overset{R}{\underset{R}{\bigg\langle}}\text{(pyrazine bicyclic structure)}(CR_2)_n$$

where R is a substituent selected from hydrogen and alkyl groups containing between about 1–12 carbon atoms; $R^1$ is a substituent selected from aliphatic, alicyclic and aromatic groups containing between about 1–20 carbon atoms; and n is an integer in the range of 1–6.

2. A smoking composition in accordance with claim 1 wherein the non-tobacco substitutes are selected from pectinaceous, cellulosic and carbohydrate materials.

3. A smoking composition in accordance with claim 1 wherein the bicyclic pyrazine is 2-acetyl-5,6,7,8-tetrahydrocyclohex[b]pyrazine.

4. A smoking composition in accordance with claim 1 wherein the bicyclic pyrazine is 2(or 3)-propionyl-5H-5-methyl-6,7-dihydrocyclopenta[b]pyrazine.

5. A smoking composition in accordance with claim 1 wherein the bicyclic pyrazine is 2-propionyl-5,6,7,8-tetrahydro-8,9,9(or 5,9,9)-trimethyl-5,8-methanoquinoxaline.

6. A smoking composition in accordance with claim 1 wherein the bicyclic pyrazine is 2-propionyl-5H,6,7,8,9-pentahydrocyclohepta[b]pyrazine.

7. A smoking composition in accordance with claim 1 wherein the bicyclic pyrazine is 2-cyclohexanoyl-5,6,7,8-tetrahydroquinoxaline.

8. A smoking composition in accordance with claim 1 wherein the bicyclic pyrazine is 2-benzoyl-5,6,7,8-tetrahydroquinoxaline.

9. A method of preparing a smoking composition which is adapted to impart flavoring to the mainstream and sidestream smoke under smoking conditions, which method comprises incorporating into natural tobacco, reconstituted tobacco, non-tobacco substitute or mixtures thereof between about 0.00001 and 2 weight percent, based on composition weight, of acylpyrazine flavorant additive corresponding to the formula:

$$R^1-\underset{\underset{O}{\parallel}}{C}-\overset{R}{\underset{R}{\bigg\langle}}\text{(pyrazine bicyclic structure)}(CR_2)_n$$

where R is a substituent selected from hydrogen and alkyl groups containing between about 1–12 carbon atoms; $R^1$ is a substituent selected from aliphatic, alicyclic and aromatic groups containing between about 1–20 carbon atoms; and n is an integer in the range of 1–6.

* * * * *